United States Patent
Bublewitz et al.

(10) Patent No.: US 6,837,612 B2
(45) Date of Patent: Jan. 4, 2005

(54) DEVICE FOR MIXING TWO PASTE-LIKE COMPOUNDS, IN PARTICULAR FOR MIXING A DENTAL-MOLDING COMPOUND WITH A CATALYZING COMPOUND

(75) Inventors: Alexander Bublewitz, Herborn (DE); Mattias Suchan, Hachenburg (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 0 days.

(21) Appl. No.: 10/331,743

(22) Filed: Dec. 30, 2002

(65) Prior Publication Data
US 2003/0123323 A1 Jul. 3, 2003

(30) Foreign Application Priority Data
Dec. 28, 2001 (DE) .......................... 101 64 385

(51) Int. Cl.⁷ ................ B01F 5/04; B01F 7/00
(52) U.S. Cl. ................ 366/172.1; 366/312; 366/326.1; 366/329.1; 222/145.6
(58) Field of Search .................. 366/172.1, 172.2, 366/176.1, 181.5, 312, 325.1, 325.2, 326.1, 329.1, 329.2; 222/145.5, 145.6

(56) References Cited

U.S. PATENT DOCUMENTS

| | | | | | |
|---|---|---|---|---|---|
| 3,051,455 A | * | 8/1962 | Magester | ................ | 366/172.1 |
| 3,302,832 A | * | 2/1967 | Anderson et al. | ............. | 222/94 |
| 3,390,814 A | * | 7/1968 | Creighton, Jr. et al. | ..... | 222/137 |
| 3,570,719 A | * | 3/1971 | Schiff | ......................... | 222/137 |
| 3,587,982 A | * | 6/1971 | Campbell | .................... | 241/62 |
| 3,767,085 A | * | 10/1973 | Cannon et al. | ............... | 222/82 |
| 4,107,793 A | * | 8/1978 | Wallace | ...................... | 366/312 |
| 4,432,469 A | * | 2/1984 | Eble et al. | .................. | 222/134 |
| 4,471,888 A | * | 9/1984 | Herb et al. | .................. | 222/137 |
| 4,767,025 A | * | 8/1988 | Gebauer et al. | ............ | 222/135 |

(List continued on next page.)

FOREIGN PATENT DOCUMENTS

| | | | |
|---|---|---|---|
| DE | 4235736 C1 | * | 3/1994 |
| DE | 298 18 499 | | 4/2000 |
| DE | 10043489 A1 | * | 3/2004 |
| EP | 0087029 A1 | * | 8/1983 |
| EP | 0 492 412 | | 12/1991 |
| EP | 0 584 428 | | 8/1992 |
| EP | 0 644 153 | | 9/1994 |
| EP | 0 885 651 | | 6/1997 |
| EP | 1110599 A1 | * | 6/2001 |
| JP | 6-226178 | * | 8/1994 |
| JP | 8-187727 | * | 7/1996 |
| WO | 98/43727 A1 | * | 10/1998 |
| WO | 01/24919 A1 | * | 4/2004 |
| WO | 02/074426 A1 | * | 9/2004 |

Primary Examiner—Charles E. Cooley
(74) Attorney, Agent, or Firm—Collard & Roe, P.C.

(57) ABSTRACT

A device for mixing two paste like compounds, such as a dental molding compound using a catalyst for the acceleration of polymerization. The housing has a mixing area with at least two inlet openings for the compounds and an outlet opening for the mixed compound. The device also has a mixing element that is disposed in the mixing area and propelled around a longitudinal axis. The housing has a coupling section that is situated in front of the mixing area with two coupling openings for connecting with two dispensing openings of a device for dispensing the two paste like compounds. The first and second ducts connect to the couplings via the coupling openings extending through the coupling section into the inlet openings for the mixing area. The two ducts are formed so that the first duct requires a greater time of entry of the compound into the mixing area than the time required for the second compound flowing through the second duct.

25 Claims, 4 Drawing Sheets

U.S. PATENT DOCUMENTS

| | | | |
|---|---|---|---|
| 4,934,827 A | * | 6/1990 | Taschke et al. ........... 366/162.3 |
| 4,951,843 A | * | 8/1990 | Paetow .................... 222/145.6 |
| 5,249,862 A | | 10/1993 | Herold et al. |
| 5,487,606 A | | 1/1996 | Keller |
| 5,503,657 A | | 4/1996 | Bouard et al. |
| 6,135,631 A | | 10/2000 | Keller |
| 6,244,740 B1 | * | 6/2001 | Wagner et al. ............ 366/181.5 |
| 6,311,871 B1 | * | 11/2001 | Binder .................... 222/145.6 |
| 6,352,177 B1 | * | 3/2002 | Bublewitz et al. ............. 222/82 |
| 6,394,643 B1 | * | 5/2002 | Bublewitz et al. ........ 366/172.1 |
| 6,443,612 B1 | * | 9/2002 | Keller ......................... 366/307 |
| 6,457,609 B1 | * | 10/2002 | Keller ......................... 222/137 |
| 6,523,992 B1 | * | 2/2003 | Bublewitz et al. ........ 366/172.1 |
| 6,530,685 B1 | * | 3/2003 | Muhlbauer et al. ......... 366/336 |
| 6,540,395 B2 | * | 4/2003 | Muhlbauer et al. ......... 366/307 |
| 2001/0005338 A1 | * | 6/2001 | Muhlbauer et al. ......... 366/307 |
| 2003/0137898 A1 | * | 7/2003 | Wagner et al. ............ 366/172.1 |
| 2004/0085854 A1 | * | 5/2004 | Pauser et al. |

* cited by examiner

DEVICE FOR MIXING TWO PASTE-LIKE COMPOUNDS, IN PARTICULAR FOR MIXING A DENTAL-MOLDING COMPOUND WITH A CATALYZING COMPOUND

BACKGROUND

The invention relates to a device for mixing two paste-like compounds for a dental-molding compound and a catalyst for the acceleration of polymerization. The device has a housing, which has a mixing area with at least two inlet openings for the two paste-like compounds and an outlet opening for the mixed paste-like compound. The device also has a mixing element that is arranged so that it can be especially propelled in the mixing area and is pivotable in the housing along its longitudinal axis. The housing also has a coupling section that is situated in front of the mixing area with two coupling openings for connecting with two dispensing openings of a device for dispensing the two paste-like compounds. A first and a second duct connect to the coupling openings, extending through the coupling section to the inlet opening for the mixing area. The two ducts are formed so that the time needed for the entry of the paste-like compound into the coupling opening of the coupling section, until the entry into the inlet opening of the mixing area of the housing, is greater for the first duct than for the second duct.

The device is attached to the two outlet supports of a delivery device, wherein the compounds to be mixed are inserted into the mixing device by applying pressure to the compounds. After these compounds are mixed in the mixing device, they are dispensed from this device as one compound.

In numerous technical application areas it is necessary to apply two separately stored paste-like compounds in a mixed form. Here either a dynamic or a static flow mixer is used such as a mixer with a moveable or stationary mixing element, which mixes the compounds with each other while flowing through the mixing housing.

A dynamic mixer is known from U.S. Pat. No. 5,249,862. This known device has a mixer housing that is essentially tube-shaped with a pivotable mixer element arranged in it. The mixer element has a number of radially protruding rib-like mixer arms that rotate around the flow of compounds, and thus mixes the two paste-like compounds with each other when the mixer element is driven. The paste-like compounds reach the mixer element via a radial front wall at the back end of the mixer housing. Thus, the front wall has two inlet supports, which are attached to the outlet supports of the device for yielding the paste-like compounds.

However, regardless of whether a static or dynamic mixer is used, the above devices encounter problems because of the uneven flow of the different mixing components and thus the uneven amounts of the components in the mixing region.

It is already known that the problem can be constructively dealt with by having the base component or components within the mixer that tend to overdose flow a longer way to the mixer element than the other component or catalyzing components. This flow is between the reserve receptacle and the mixer. A first example for such a concept is described in DE-U-298 18 499, according to which the duct of the one component runs in the form of an arch around the longitudinal axis of the pivotable mixer element between the inlet of a dynamic mixer to the actual mixer area. An example for solving the problem in the case of a static mixer is given in U.S. Pat. No. 6,135,631, whereby this mixer was already on the market before the application date of the subject of DE-U-298 18 499, and was freely distributed and disbursed to third parties. Also for these known static mixers, the base component that tended to overdose was redirected in an arch-like form in the mixer, and the flow of compounds was divided in two, to reach the stationary mixing element next to the compound flow of the other component or other catalyzing component. In so doing, the introduction of the non-advancing (catalyzing) component flows as directly as possible, i.e. without any detours that would increase the flow resistance. Further examples for such mixers which delay the advancement of faster flowing compounds serving as dead volume are known from U.S. Pat. No. 5,487,606, and EP-A 0664 153.

In the case of the known mixers, a recontamination can occur after the deploying process ends, such as when the application device is shut off. This can occur because the base component flows into the container of the catalyzing component due to the varying pressure in the reserve receptacles of the paste-like compounds. If these components mix with each other and polymerize or harden in the deploying duct of one of the reserve receptacles of the paste-like compounds, the entire reserve receptacle and its content are unusable.

The present invention provides an additional device for mixing two paste-like compounds, whose mixing ratio is constant from the beginning of the dispensing of the mixed compounds, and also prevents a recontamination of these two compounds.

SUMMARY OF THE INVENTION

Thus, this device includes two ducts which are formed so that at least the first duct has a first segment that extends from the coupling opening in an axial direction of the mixer element, and a redirecting section that is connected to this. There is also a second segment leading to the associated inlet opening, whereby the axes of the first and second segments lie on a common level with the longitudinal axis of the mixer element.

Moreover, in addition to this, the two ducts are formed so that at least the first duct has a segment that extends from the coupling opening in the form of an arch around the axis of the mixing element. A second segment is provided which is placed in axial direction of the mixing element to the first segment, and leads to the associated inlet opening. There is a redirection segment that connects the first and the second segment. The redirection segment is arranged further away from the coupling opening, and serves as the inlet opening.

Basically, the temporary initial excess of the prescribed dosage or overdosage of one of the two components or compounds is compensated for by a corresponding form of the duct through which this compound flows until it arrives at the mixer element. This compensation occurs so that the paths, and thus also the retention periods vary the time the paste-like compounds need from the entry into the coupling openings of the coupling section of the mixer housing, to the entry into the inlet openings of the tube-shaped section of the mixer housing. It can be determined, from a study of the overdose amount and, if need be, of the flow speeds of both of the components to be mixed, how to form one of the two or both ducts by changes, such as via cross sectional changes, or form and size changes, as well as changes in length of the duct or ducts, so that both components simultaneously arrive in the inlet openings of the tube-shaped section of the mixer housing.

Beyond that, the invention also overcomes this problem by providing a second duct that has an extension section that lengthens the path between the coupling's opening and the associated inlet opening. This lengthening or extension section in certain areas, can be in the form of an arch around the longitudinal axis of the mixer element. In addition, the lengthening section has a first segment extending from the coupling opening in an axial direction of the mixer element, and a redirection section connected to this section, and a second segment that leads to the associated inlet opening, whereby the axes of the first and the second segments lie at a common level with the longitudinal axis of the mixer element. The lengthening section can extend, for example, 90° or 45° around the longitudinal axis of the mixer element in the form of the second duct that runs in an arch shape around the longitudinal axis of the mixer element. The occurrence of recontamination could also be avoided, even with an arch-shaped redirection of only approximately 5°. The entry of the (catalyzing) component in the mixer area is delayed by redirecting the paste-like compound in the second duct. To prevent an underdosage of the (catalyzing) component in the initial phase, the path of in the first duct can be lengthened, or by increasing the corresponding time which the paste-like (basis) compound requires from its entry in the coupling opening of the coupling section to its entry in the inlet opening of the mixer area of the housing. The redirecting in the second duct at the same time, increases the flow resistance in the second duct to prevent a recontamination by the base compound flowing into the second duct from the first duct, which would otherwise occur at the end of the deploying process, for example, when the application device is shut off. Thus, a mixing and hardening (polymerization) of the two components consequently cannot occur in the area upstream from the coupling opening, which is the device that dispenses the two paste-like compounds.

To compensate for the overdosage of one flow of compounds, the (first) duct assigned to this compound is designed to have a longer flow than the other (second) duct. This lengthening is achieved by extending the pertinent duct initially from the inlet opening of the coupling section of the mixer housing in the axial direction of the mixer element, or is formed as an arch around the axis of the mixer element. This duct is then a redirected preferably 180° and extends subsequently in the axial direction of the mixer element, or in the form of an arch around the axis of the mixer element, so that it ends, after being redirected 90° to 180° in the inlet opening of the mixer area. This form of the duct saves space while still providing a tolerable flow resistance. At the same time, as a result of these designs of the duct, the inlet opening of the mixer area is situated close to the coupling opening. When the coupling openings are arranged at 180° to each other, the inlet openings lie far from each other so that this recontamination is prevented. Moreover, the increased flow resistance in the other or second duct can be compensated for by this duct design where the duct includes a lengthening section to avoid any recontamination.

The duct formed in accordance with the invention can also be divided into two or several duct segments respectively that are basically parallel or, in particular, with regard to their path, formed the same. In other words, the coupling section of the housing of the mixer in accordance with the invention has ducts of various lengths that lead to the entry openings of the tube-shaped housing section. Alternatively, the two ducts can also have a varying sized dead volume, which is designed in accordance with fluid mechanics so that the compound only continues to flow in the direction of the inlet opening assigned to the pertinent duct, only after filling the pertinent dead volume. Instead of furnishing both ducts with dead volume, it is also possible to form only one of the two ducts with a dead volume.

In practice, mixers that are attached to two outlet supports of an application device are arranged at intervals to each other, to function properly. The mixer housing has thus in its coupling section, two coupling openings, which are axially staggered to the mixer element, and arranged diametrically opposite to each other. The inlet openings of the tube-shaped section of the mixer housing for the known mixers also lie, as a rule, diametrically opposite one another. Thus, for the known mixer designs, short ducts result between the coupling openings and the inlet openings assigned to them. The redirecting of at least one (or base) compound along segments of the first duct occurs so that ducts of varying lengths can be formed with such a mixing concept, whereby the axis of the first duct lies at a common level with the axis of the mixer element, or is in the shape of an arch around the longitudinal axis.

The arrangement of the segments of the first duct are formed so that the longitudinal axes of the segments together with the longitudinal axis of the mixer element span a joint radial level, and has the advantage of providing a space-saving form of the longer first duct. The segments of the first duct are preferably formed linearly. Alternatively, it is also possible that the ducts can be formed curvilinear or curved. However, in this case the curved longitudinal axis are arranged in turn in a joint radial level together with the (linear) longitudinal axis of the mixer element.

In the case described above, in which the segments of the first duct are formed linearly, it is furthermore advantageous if they run parallel to each other. The redirecting section is formed U-shaped in this case, for example, extending over 180°.

If the segments of the first duct extend in the form of an arch around the longitudinal axis of the mixer element, for example, they are formed over each other in an axial direction, wherein the redirection section is formed C-shaped, or it extends over 180°. In so doing, the compound flows at first in the first segment in the shape of an arch away from the coupling opening, and after redirecting, led back toward the inlet opening, which preferably lies near to the coupling opening. This design of the first duct is particularly space saving.

The inlet openings of the two ducts into the mixing area can lead axially or radially into the mixer element. An additional redirection section can still be connected to the second segment whichever form of the alignment of the inlet openings is used. This additional redirection section extends by 90° when the two segments of the first duct are aligned parallel, if the inlet openings discharge radially into the mixing area. This redirection extends over a total of 180° if the inlet openings discharge axially into the mixing area.

In another embodiment, the mixer element has at least one redirection element for support of the transport of the paste-like compounds in axial direction. These compounds arrive through the inlet openings into the tube-shaped section of the housing. At this point, the redirection element has a redirection surface that extends around the axis and runs inclined to the radial level of the axis. In this embodiment, compounds are fed radially in the essentially tube-shaped section of the mixer housing. Thus, the tube-shaped section of the housing has two radial inlet openings that are disposed diametrically opposite one another. The flows of paste-like compounds, which are inserted by applying pressure into the mixer, encounter at least one redirection element that extends around the axis of the mixer element within the tube-shaped section of the housing. This redirection element rotates with the revolving mixer element, and has a redirection surface that runs diagonally to the radial level of the axis. In other words, at least one redirection element has an essentially saw-tooth-shaped wedge that bends around the axis of the mixer element. This redirection element functions like a conveying screw for a spiral pump, and ensures that the upcoming paste-like material is directly transported in the axial direction from the inlet openings toward the outlet opening. Thus, recontamination continues to be prevented since the redirection element supports the axial feeding of the paste-like compounds arriving through the inlet openings in the tube-shaped section of the mixer housing.

The redirection element can have a wedge form. Alternative to this wedge form, the redirection element can be formed as a ridge that runs in the shape of a helix around the axis. In this embodiment, the redirection element thus has the form of a screw thread. These circumferential ridges are known from spiral pumps and conveying screws.

Two redirecting elements are advantageously arranged on the axis at the level of the radial inlet openings of the mixer area of the housing. The redirecting elements are diametrically arranged opposite to each other. These redirecting elements or every redirecting element extends preferably across an angular range of 180° to 90°.

The housing has an insertion aligned transversely to the axis on its back end, from which two inlet supports protrude. These inlet supports connect the mixer to the two outlet supports of a squeezing device. The insertion is in a conically widened section of the housing that is connected to the mixer area. It has two ducts that extend from the inlet supports. These two ducts run under, bending radially in a concentric cylindrical intake recess on the inner side of the insertion, by which the axis of the mixer element is taken in with at least the one redirecting element. Thus, the cylindrical intake recess of the insertion forms a subarea of the mixer area. The two inlet supports of the insertion form the couplings openings, and are connected to the outlet supports of the delivery or squeezing device. Thus, it is possible that the outlet supports are connected to the inlet supports.

However, unlike the previous embodiments, the two ducts extend then to the mixer element. Thus, the duct which extends from that inlet support, through which the compound material flows with the overdosage, at the beginning of the operation of the delivery device, is divided into two or more partial ducts that preferably at first, extend in the circumferential direction around the cylindrical intake recess, in two or more of these inlet openings, assigned respectively to these partial ducts.

The form of the mixer is such that several ducts extend from one or both coupling openings. The ducts end in several inlet openings, which discharge particularly uniformly in the section of the mixer housing with the mixer element. In addition to the improved fluidic performance of the paste-like compounds, it has the advantage that the materials admitted into the mixing area can be better and more homogeneously mixed. The spatially distributed insertion of each of the two compounds or at least of one of the two compounds, contributes to this because this distributed insertion of both compounds or at least of one of the two compounds in the mixer area has the advantage that a sort of premixing takes place through the portioning of the compounds flow into several inlet openings.

The individual partial ducts can be of the same or different length. They can be formed in the shape of a collective duct departing from the related coupling opening. Several diverging ducts branch off from the collective duct and they end in the inlet openings.

This concept of the spatially distributed feeding of the flows of compounds in the mixing area is applicable independent of whether the inlet openings are now arranged radially or axially. In other words, the normal lines of the opening cross sections of the inlet openings can be arranged both in the direction of the longitudinal extension of the mixer element, and also radially.

Also, the concept described above of the constructive design of the mixer, provides that both of the compounds arrive at the same time in the mixer area despite a possible occurrence of excessive flow rate of one of the two compounds, especially at the start of the material delivery. This result can likewise be achieved independent of whether the normal lines of the inlet openings run radially or parallel to the mixer element, or in another angle to it.

The invention has the benefit that several mixer arms are in the tube-shaped housing section between the radial inlet openings and the axial outlet opening. These arms protrude like a type of radial ribbing from the axis, and reach close to the inner surface of the tube-shaped housing section. These mixer arms are arranged within several radial levels from the shaft, and lead to a redirecting of the compounds flows that extend axially through the housing. Thus the desired mixing occurs through this. The mixing effect is further strengthened if these mixing arms, which due to their radial alignment, prevent the direct flow between the inlet openings and the outlet opening, and extend to a larger angular range, for example 90°. This can be achieved if adjacent mixer arms are connected to each other by a circumferential segment. In this way, therefore, mixer arms result that are formed like a type of quarter circles, whereby it can also be favorable if these quarter circles in their middle sections, as viewed in the circumferential direction, are more distant from the inner surface of the tube-shaped section of the housing in relation to their ends. It is practical if, from a first radial level to a second radial level, offset in the circumferential direction, two adjacent radial running mixer arms are respectively connected to each other in the way described above.

In addition to the rigid mixer arms, it is also advantageous for the thorough mixing process if the mixer element has additional flexible wiper elements, which sweep along at the inner wall of the tube-shaped housing due to their flexibility, or at least on the basis of their flexibly formed free end, are spaced from the axis. Alternatively, the wiper elements can also be formed rigidly and be tangentially distant from the axis of the mixer element. Two arranged rigid wiper elements are then arranged diametrically opposite to two different radial levels of the mixer element. Finally, it is also possible to provide for flexible and rigid wiper elements jointly at the mixer element.

In a further advantageous embodiment of the invention, the mixer arms of the adjacent first radial levels, which are in the axial direction to the inlet openings of the tube-shaped section of the housing, are shorter than the mixer arms in the remaining second radial levels. Thus, the distance between the radial outlying ends of the mixer arms to the tube-shaped housing section within the first radial levels is greater than within the second radial levels. This leads to a larger mixer area in the area of the tube-shaped housing section, which connects to the inlet openings. This larger mixing area has the advantage that dosage tolerances conditioned by the squeezing or delivery device are better compensated. The material component moving ahead has a longer retention period in the mixing area through the additional arrangement of the tangentially distant wiper elements within this enlarged mixing area. Through this, more time is available for mixing the slower material component with the material component moving ahead.

A larger mixing area in the area described before is however advantageously achieved when the axis of the mixer element is smaller in diameter than the remaining area, and the mixer arms extend radially, precisely as far as all other mixer arms, namely directly to the inner side of the tube-shaped housing section.

BRIEF DESCRIPTION OF THE DRAWINGS

Other objects and features of the present invention will become apparent from the following detailed description considered in connection with the accompanying drawings which disclose the embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION

Figure 1:
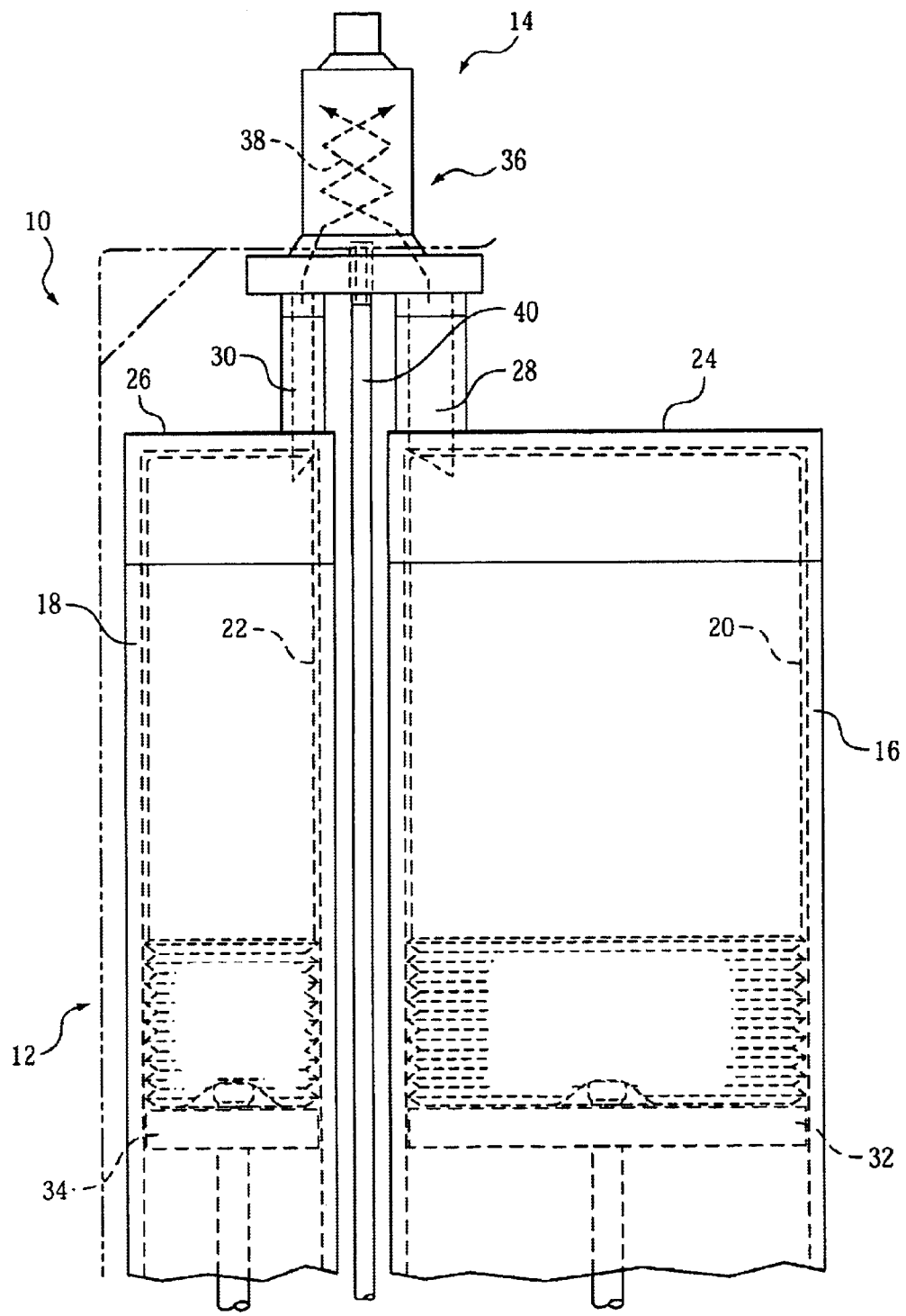
FIG. 1 is a side cross sectional view of a delivery device for mixed components.

Referring in detail to the drawings, FIG. 1 shows a delivery device 10 that is displayed in a side view for two paste-like components that are to be mixed with one another. Device 10 comprises a squeezing part 12, and a mixer part 14, whereby squeezing part 12 has two pressure tanks 16, and 18 for receiving tubular bags 20, and 22 containing the two paste-like compounds. At the forward frontal ends 24, and 26 of pressure tanks 16, and 18, these dispensing openings have outlet supports 28, and 30. By applying pressure to the back end of tubular bag 20, and 22 its contents are delivered through outlet supports 28 and 30. The pressure impact of tubular bag 20, and 22 occurs via pressure pistons 32, and 34, which are driven by a motor not shown.

A dynamic mixer 36 is attached to outlet supports 28, and 30. Dynamic mixer 36 is shown in FIGS. 2–7. Dynamic mixer 36 has a motor that drives mixer element 38. Mixer element 38 can be coupled with a driving bar 40 that is rotatably driven by a motor that is also not shown. It is possible in the same way to attach a mixer 36' or 36" shown in the FIGS. 8 or 9 to outlet supports 28, and 30 of device 10.

Figure 2:
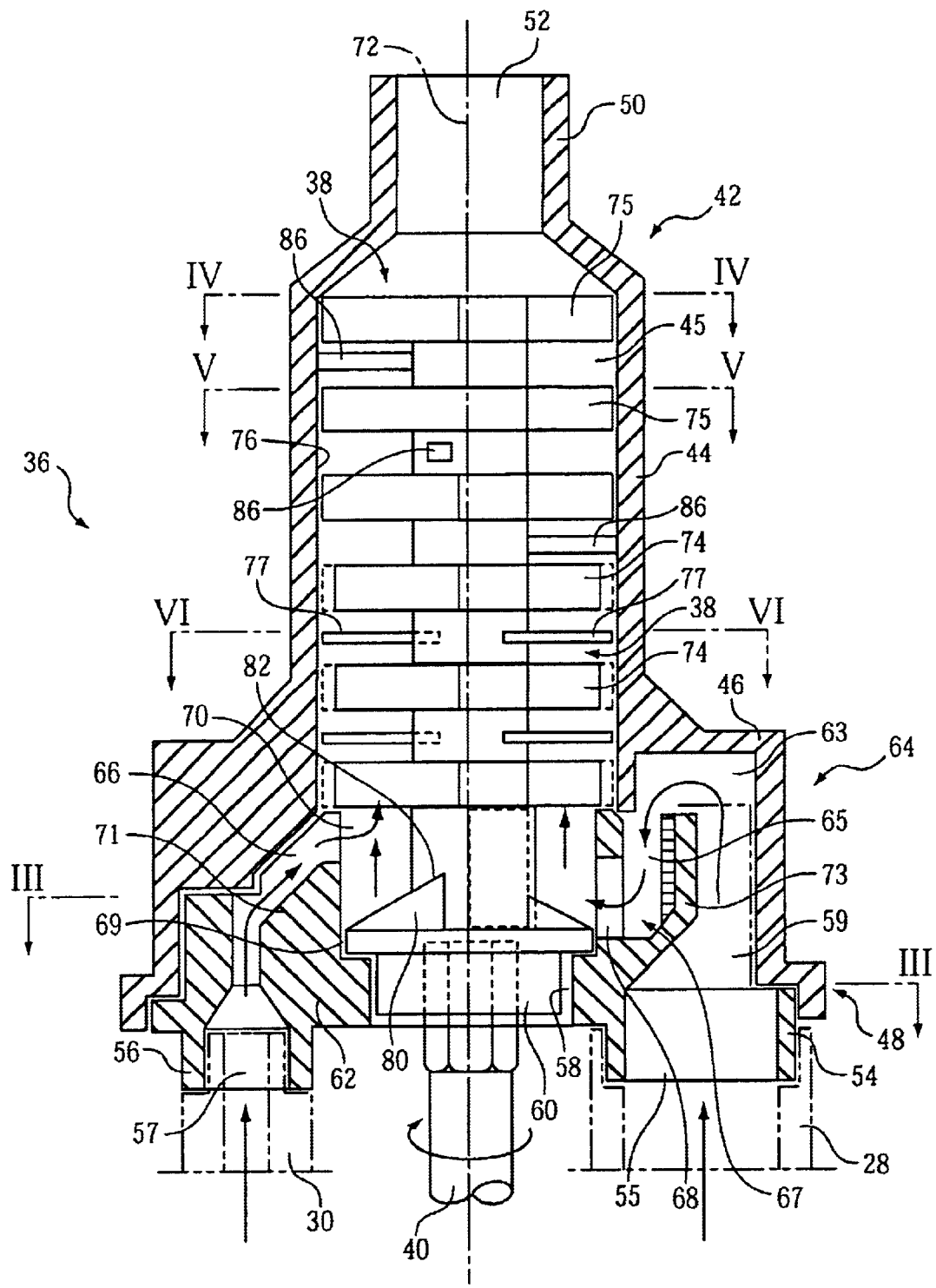
FIG. 2 is a cross sectional view of a dynamic mixer wherein the dynamic mixer is used as a delivery device for the embodiment shown in FIG. 1.

Dynamic mixer 36 is shown in greater detail in FIG. 2. FIG. 2 shows a longitudinal cut through mixer 36. Mixer 36 has a housing 42 that comprises an essentially cylindrical or tube-shaped section 44, which defines a mixer area 45, in which mixer element 38 is arranged. Moreover, housing 42 has a conically widened coupling section 46 connected to tube-shaped section 44. Conically widened coupling section 46 is turned toward squeezing part 12 at a back end. Mixer 36 also has a tapered forward end 50 opposite this back end 48. Tapered forward end 50 is formed as outlet supports and defines outlet opening 52 for the material mix, while at back end 48 of housing 42, two inlet supports 54,56 are arranged that form coupling openings 55 and 57 and can be attached to outlet supports 28, and 30 of squeezing part 12. Between two inlet supports 54, and 56 is an opening 58, in which one end 60 of mixer element 38 is pivoted. Driving bar 40 can be coupled with mixer element 38 through this opening.

Inlet supports 54,56 and opening 58 are formed by an insertion 62 that is inserted at back end 48 of housing 42 in its conical coupling section 46. Departing from inlet supports 54, and 56, two ducts 64, and 66 extend through insertion 62. These two ducts 64, and 66 meet through a redirection in radial openings 68, and 70. These inlet openings 68, and 70 are radially arranged with regard to section 44 of housing 42. The two paste-like components are delivered into dynamic mixer 36 through ducts 64, and 66. There the paste-like components meet in the radial direction of mixer element 38.

Figure 3:
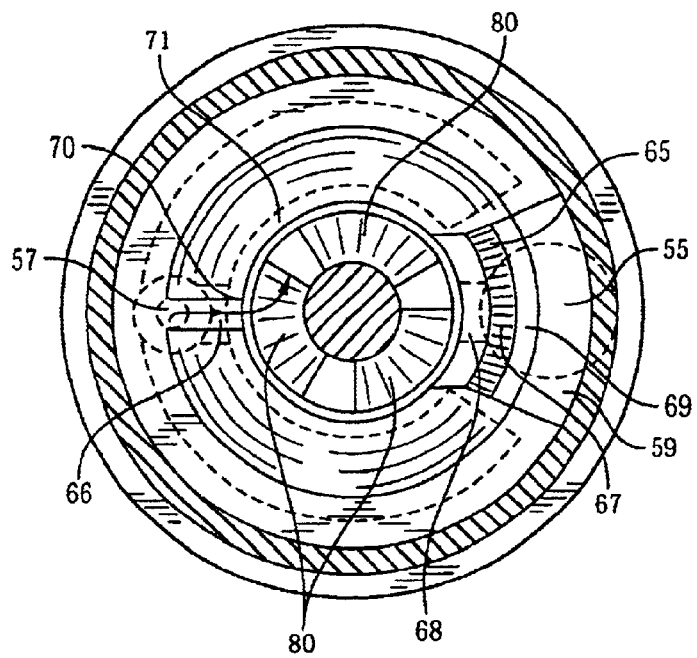
FIG. 3 is a cross-sectional view of the mixer shown in FIG. 2 taken along the line III—III.

FIGS. 2 and 3 show that insertion 62 has an intake recess that is central and essentially cylindrical. This intake recess is arranged concentric to opening 58 and inserted in mixer element 38. Inlet openings 68, and 70 are inserted in cylindrical wall 71 of intake recess 69. Furthermore, ducts 64, and 66 are also formed in this area. These ducts 64,66 are formed as grooves open above, or notches, which together with the essentially conically widened coupling section 46 form a duct closed on all sides.

FIG. 2, shows first duct 64 is divided into several diversely running sections. Thus, first duct 64 has a first segment 59 that connects to coupling opening 55. First segment 59 extends in an axial direction of mixer element 38. At the end of this first segment 59 is a U-arch-shaped redirecting section 63, which gives way to a second linear section 65. From this, it goes through a further redirecting section 67, which is essentially a 90° arch, before ending in inlet opening 68. Two segments 59 and 65 extend parallel to each other, whereby their two parallel longitudinal axes run in a joint radial level to longitudinal axis 72. The special essentially S-shaped form of first duct 64 is formed by an interaction between housing 42 and a protruding wall element 73 of insertion 62.

Duct 64 extends first in the direction of outlet opening 52 and afterwards is redirected in order then to run back toward the back end of mixer 36. This design is a direct route instead of the second duct 66 departing from its coupling opening 57 and flowing directly radially into inlet opening 70. Thus, duct 64 can be given a longer length than duct 66. Thus, in other words, a dead volume results due to the additionally created duct volume, which first has to be filled so that the flowing compound can flow further into the inlet opening 68. Thus overdosages of the compound flowing through this duct can be corrected.

Mixer element 38 has a pivoted axis 72, from which four rib shaped mixer arms 74, and 75, respectively, essentially radially protrude in a multitude of radial levels. The exact arrangement of these mixer arms 74, and 75 results from the sectional view according to FIGS. 4 to 6. A limiting lateral edge of mixer arms 74, and 75, which lies in the circumferential direction, runs essentially tangentially to the peripheral surface of axis 72. Furthermore as viewed from the flow direction, first mixer arms 74 are shorter than second mixer arms 75 arranged turned toward outlet opening 52. Thus, the radial distance out from mixer arms 74 to inner surface 76 of tube-shaped section 44 is thus greater than in the case of mixer arm 75. Thus, viewed from the flow direction of the compound, a mixing area section within housing 42 follows inlet openings 68, and 70. This mixing area section is larger than the mixing area section, in which longer mixer arms 75 are arranged. Between adjacent radial levels of mixer arms 74, moreover, tangentially protruding wiper elements 77 are arranged, which contribute to an improvement of the mixing. The larger first section of the mixer area with regard to volume, moreover, assures that, as needed, the one leading compound also has a longer retention period in the mixer area, so that enough time remains for the other slower flowing compound to mix homogeneously with the compound first mentioned.

FIG. 2 shows a variation of the mixer which is indicated with dashed lines. With this variation, axis 72 is thinner in the area of the first radial level than within the remaining radial levels. Mixer arms 74, and 75 have all the same extension, namely, directly contiguous to housing section 44.

Figure 4:
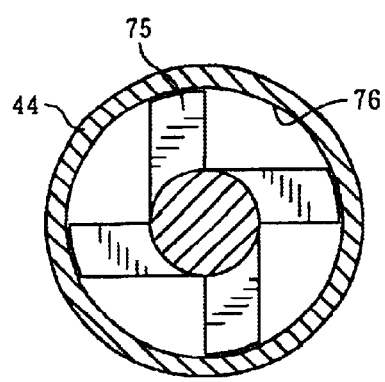
FIG. 4 is a cross-sectional view of the mixer shown in FIG. 2 taken along the line IV—IV.
Figure 5:
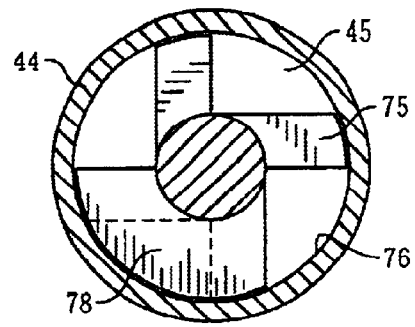
FIG. 5 is a cross sectional view of the mixer shown in FIG. 2 taken along the line V—V.
Figure 7:
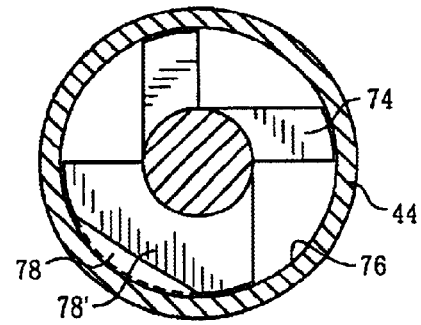
FIG. 7 is a cross sectional view similar to the view shown in FIG. 6, showing an alternative form of the mixer element.

FIG. 4 shows four mixer arms 74 that are disposed on each radial level. Mixer arms 75, reach according to FIG. 3 to a region contiguous to inner surface 76 of housing section 44. The total area between inlet openings 68, and 70 and the end of mixer element 38, extends to tapered end 50 of housing 42. In addition, mixer element 38 has mixer arms 78 formed like a quadrant. These mixer arms 78 are formed by connecting two adjacent mixer arms 74 in a radial level. In this embodiment, the radially outlying limiting edge of mixer arm 78 is formed in the shape of circular arc, while it runs with the alternative according to FIG. 7 secantially. FIG. 7 shows mixer arm 78' which therefore has in a middle circumferential section a larger distance to inner surface 76 of housing section 44.

As shown in FIG. 7, mixer arms 74, 78, and 78' assure a redirecting and thus turbulence of the axially flowing paste-like compounds due to their radial extension close to housing section 44 with the rotation of mixer element 38, mixer element 38 has three redirecting elements 80 in the area of the radial inlet openings 68, and 70 that are arranged uniformly offset by 120° to each other and are formed like a type of conveying screw. Redirecting elements 80 are formed as sawtooth-shaped wedges that extend to approximately 60° around axis 72 of mixer element 38. As shown in FIG. 2, redirecting elements 80 have a redirecting surface 82 that rises in the circumferential direction. Redirecting surface 82 points toward outlet opening 52 of dynamic mixer 36 and runs angled to a level radial to axis 72. These redirecting elements 80 run therefore sectionally in the form of a helix and assure an axial movement component of the paste-like compound flows along longitudinal axis 72. Thus, redirecting elements 80 support the delivery of the paste-like compound, which enters from inlet openings 68, and 70 into housing section 44. This supporting and thus strengthening discharging of the paste-like compound in the axial direction reduces the danger of contamination of the two paste-like compounds, which is the undesired mixing or recontamination of the two paste-like compounds through inlet opening 68, and 70 in ducts 64, and 66 possibly further in outlet supports 28, and 30. If there is a contamination and thus a polymerization in these areas, the residual material that may still be in tubular bags 20, and 22 can no longer be delivered due to stoppage of outlet supports 28, and 30. Diverging from the illustration in FIG. 2 redirecting elements 80 can be formed in so that at least its back end in the movement direction extends along sufficiently far in mixer area 45 in the direction of outlet opening 52 of dynamic mixer 36 so that this extends to both inlet openings 68, and 70. The flow of compounds delivered through inlet openings 68, and 70 for improving the mixing and reducing a recontamination can be cut off for a short time or at least reduced.

In addition to redirecting elements 80, mixer element 38 has two wiper ribs 86 that lie diametrically opposite each other. These ribs are spaced radially from axis 72 of mixer element 38 and run parallel to axis 72. Wiper ribs 86 move with little clearance within along cylindrical wall 71 of insertion 62 while mixer element 38 is rotating. These wiper ribs contribute to an overall homogeneous thorough mixing of the two compound flows. FIG. 2 shows two wiper ribs 77 that connect two mixer arms 74 that lie diametrically opposite each other within the first radial level of mixer arms 74. This radial level connects to inlet openings 68, and 70, with the end of mixer element 38 arranged in opening 58 of insertion 62.

Figure 6:
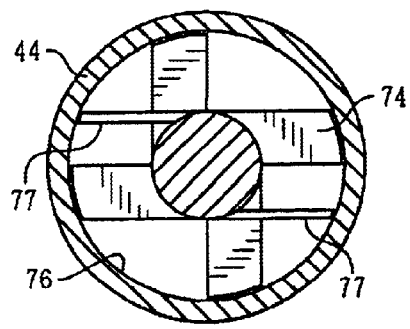
FIG. 6 is a cross-sectional view of the mixer shown in FIG. 2 taken along the line VI—VI.

FIG. 6 shows a further characteristic of dynamic mixer 36 wherein mixer arms 74 are rigid, essentially radially protruding ribs, which lead to a turbulence of the compound flows due to the rotation around axis 72. In addition to rigid mixer arms 74, and 75 and wiper elements 77, dynamic mixer 36 can have further mixer arms 86 formed like thin flexible ribs, which wipe from within along inner side 76 of housing section 44. These additional flexible mixer arms 86 assure a turbulence of the compound flow. One of flexible mixer arms 86 per level exists in several consecutive radial levels of mixer element 38, whereby these mixer arms 86 are arranged around a constant angular range offset from one radial level to another radial level. The same is true for mixer arms 78 or 78', which connect two adjacent mixer arms 74, and 75 with each other and likewise are arranged in this case displaced offset from each other by 90° from radial level to radial level. These mixer arms 86 and mixer arms 78 or 78' are therefore arranged uniformly distributed along a helix around axis 72. Both mixer arm types are excellent for a homogeneous mixing of the paste-like compounds in dynamic mixer 36, which also can be characterized as a flow path mixer.

Figure 8:
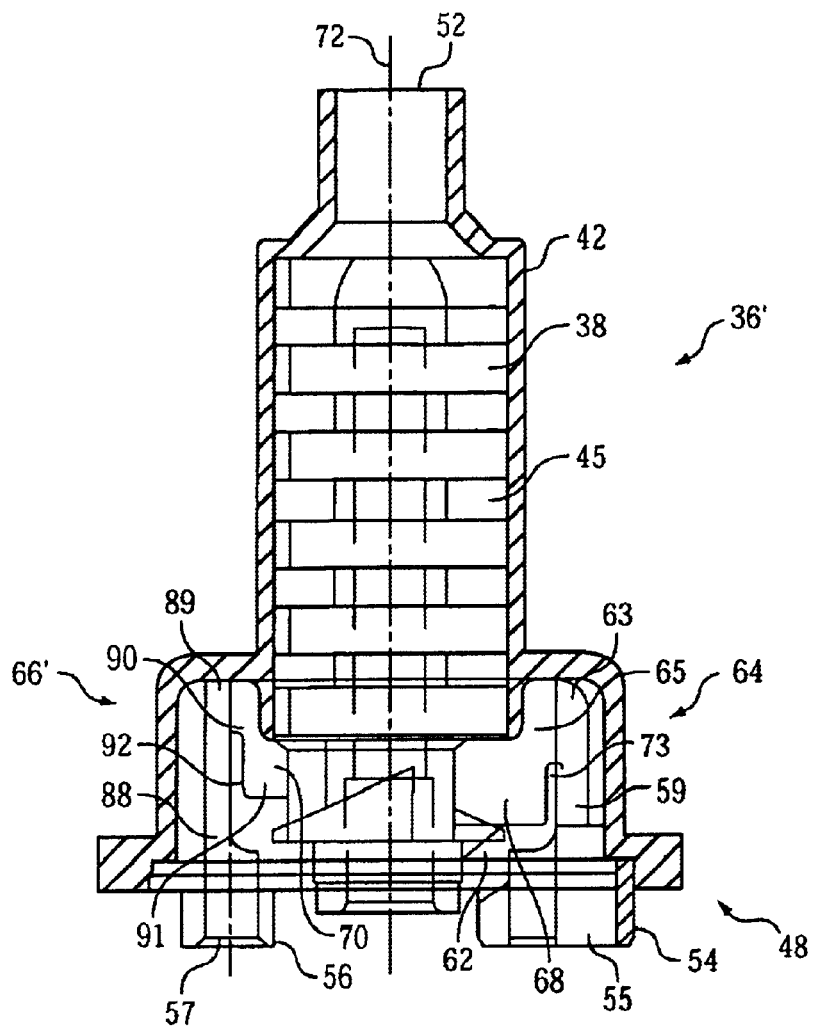
FIG. 8 is a longitudinal sectional view through the dynamic mixer shown of FIG. 2 being used with the delivery device shown in FIG. 1.

Dynamic mixer 36' shown in FIG. 8 essentially corresponds to mixer 36 shown in FIG. 2. The form of first duct 64 with a first segment 59 that connects to coupling opening 55 and extends in an axial direction of mixer element 38, with a U-shaped redirecting section 63 and with a second linear segment 65 corresponds approximately to the design of first duct 64 according to the embodiment according to FIG. 2. For this, a wall element 73 is formed in insert 62 that runs essentially parallel to longitudinal axis 72 of mixer 36'.

Thus a second duct 66' of dynamic mixer 36' is also furnished with a first segment 88 that is connected to coupling opening 57. Segment 88 extends in the axial direction of mixing element 38. At the end of this first segment 88, is a U-arch-shaped redirecting section 89 that leads to a second linear segment 90 and from this, leads through an additional redirecting section 91 that is essentially a 90° arch and ends in inlet opening 70. Redirecting section 89, second linear segment 90 and additional redirecting section 91 together form a lengthening section lengthening the way from coupling opening 57 to inlet opening 70. Two segments 88 and 90 extend parallel to each other, whereby their two parallel longitudinal axes run in a common radial level to longitudinal axis 72. The special form of second duct 66', which is essentially S-shaped, is achieved in interaction between housing 42 and a protruding wall element 92 of insertion 62.

Duct 66' is given a greater length and the flow resistance is increased because duct 66' first extends in the direction of outlet opening 52 and afterwards is redirected, so that it then runs back in the direction of back end 48 of mixer 36'. Consequently, there is a reduction in the danger of contamination of the two paste-like compounds, which results from undesired mixing or recontamination of the two paste-like compounds through inlet openings 68, and 70 in ducts 64, and 66" and may be further contaminated in the outlet supports. If there is a recontamination in these areas and thus a polymerization of the compounds, the residual material that may still be in the tubular bags can no longer be delivered, as mentioned above, due to the stoppage of the outlet supports.

The greater length of duct 66' is however compensated by the design of duct 64 described above, so that the compounds arrive through ducts 64 and 66" simultaneously via inlet openings 68 or 70 in mixer area 45.

Figure 9:
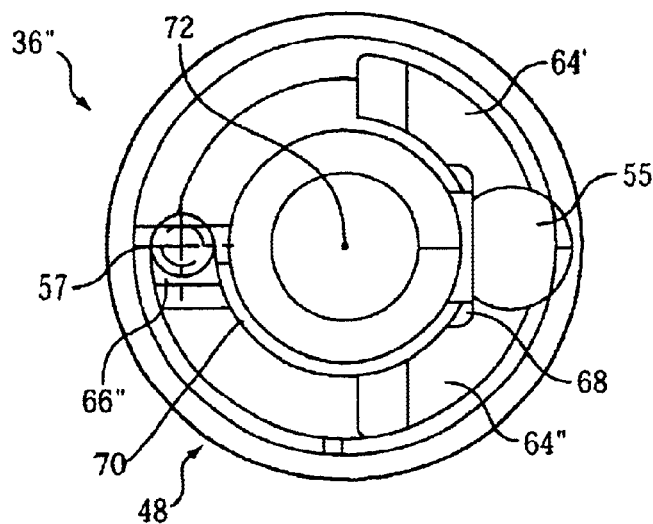
FIG. 9 is a view of the back wall of a dynamic mixer according to a third embodiment, wherein the mixer is being used with the delivery device shown in FIG. 1.

A further embodiment of a dynamic mixer 36" is shown in FIG. 9, as seen from its back end 48. Tube-shaped section 44 of housing 42 and mixer element 38 included in it corresponds essentially to the form described in FIGS. 1–8. The form of the ducts, which extend from coupling openings 55 and 57 to inlet openings 68, and 70, diverge in this embodiment.

For example, first duct, which extends between coupling opening 55 and inlet opening 68 is divided into two partial ducts 64', and 64", which extend in opposite directions in the form of an arch around longitudinal axis 72. Both partial ducts 64', and 64" have a first segment that connects to coupling opening 55. First segment extends about 45° around longitudinal axis 72. At the end of this first segment is a U-arch-shaped redirecting section, which leads to a second arch-shaped segment that extends essentially in the axial direction underneath the first segment. The two segments of partial ducts 64', and 64" can then lead to a common inlet opening 68 or into two inlet openings separate from each other. The redirection between the first and second segments occurs at about 180°, so that the partial compound flows in partial ducts 64', and 64". These ducts 64' and 64" are at first directed in the form of an arch away from the coupling opening 55 and after the redirecting in a offset level are led back to inlet opening 68 or inlet openings, which are arranged in the vicinity of coupling opening 55.

With this design partial ducts 64', and 64" are given a greater length, so that additional duct volume results. The additional duct volume must first be filled so that the compound can flow into inlet opening 68. Both compounds enter therefore approximately at the same time in mixer area 45.

Second duct 66", which extends from coupling opening 57 to inlet opening 70, also runs in the shape of an arch along longitudinal axis 72. In the embodiment shown in FIG. 9, the flowing compound is redirected in second duct 66" by about 5° around longitudinal axis 72. It is however also possible, to achieve other, in particular larger, redirections around longitudinal axis 72. It is also still possible to also form second duct 66" with two partial ducts that extend in the opposite direction in the form of an arch around longitudinal axis 72.

The length of second duct 66" is insignificantly greater as a result of the redirecting in second duct 66", while the flow resistance in second duct 66" however clearly increases. The danger of a recontamination is considerably reduced through this design.

Inlet openings 68, and 70 of the two compounds advantageously lie nearly diametrically opposite one another in the embodiment shown in FIG. 9. The path that a compound must cover before a recontamination can occur, exits from one inlet opening into the inlet opening of the other compound, which lies essentially opposite it, is consequently chosen to be as large as possible. The danger of recontamination is thus further reduced.

The designs of the first and second ducts shown in the examples can of course be combined with each other in any way desired. It is therefore possible to provide an arch-shaped redirecting of the first duct and an axial redirecting of the second duct. In the same way, an arch-shaped redirecting of the second duct can also be achieved with an axial redirecting of the first duct.

Accordingly, while at least one embodiment of the present invention has been shown and described, it is to be understood that many changes and modifications may be made thereunto without departing from the spirit and scope of the invention as defined in the appended claims.

What is claimed is:

1. A mixing device for mixing at least two compounds in a form of at least one dental mold compound and at least one catalyzing compound for communication with at least one dispensing device having dispensing opening for dispensing the at least two compounds, the mixing device comprising:
   a) a housing, having;
      i) at least one mixing area disposed within said housing and extending along A longitudinal axis;
      ii) at least one coupling section having:
         a) at least two coupling openings, comprising at least a first coupling opening and at least a second coupling opening for coupling with the dispensing openings of the dispensing device,
         b) at least two duct in communication with said at least one mixing area and comprising at least one first duct and at least one second duct, wherein said at least one first duct has a first segment that extends from said at least one first coupling opening in an axial direction substantially parallel to said longitudinal axis of said mixing area; and a redirecting segment coupled to and in communication with said first segment, and a second segment coupled to and in communication with said redirecting segment, wherein said second segment extends substantially parallel with said longitudinal axis of said at least one mixing area wherein said at least one first duct is formed to extend a flow time of at least one of the at least two compounds in relation to a flow time of at least another of the at least two compounds flowing through said at least one second duct;
      iii) at learnt two inlet openings comprising at least one first inlet opening and at least one second inlet opening with said at least two inlet openings in fluid communication with said at least one mixing area and said at least one coupling section for allowing the at least two compounds to flow from said at least one tirot duct and said at least one second duct into said at least one mixing area;
      iv) at least one outlet opening, in fluid communication with said at least one mixing area, for dispensing a mixed compound which is mixed from the at least two compounds in said at least one mixing area; and b) at least cane mixer element disposed in said mixing area of said housing said at least one mixer element being pivotable about said longitudinal axis of said mixing area;

wherein the at least two compounds are dispensed from the at least one dispensing device through the dispensing openings into said at least two coupling openings through said at least two ducts and said at least two inlet openings wherein the at least two compounds are mixed in said at least one mixing area by said at least one mixer element and then dispensed through said at least one outlet opening.

2. The mixing device as in claim 1, wherein said at least one second duct further comprises a lengthening section lengthening a flow path from said at least one second coupling opening to said at least one second inlet opening.

3. The device as in claim 2, wherein said at least one lengthening section has at least one section that extends in a form of an arch around said longitudinal axis of said at least one mixing area.

4. The device as in claim 2, wherein said lengthening section comprises:
    a tirot segment that extends from said at least one second coupling opening in an axial direction of said mixer element;
    a redirecting segment that is coupled to and in communication with said first segment;
    a second segment that is coupled to and in communication with said redirecting segment wherein said second segment leads into said at least one second inlet opening, wherein said first segment and said second segment extend parallel to said longitudinal axis of said mixing area.

5. The device as in claim 1, wherein said first segment and said second segment of said at least one first duct run parallel to each other.

6. The device as in claim 1, wherein at least one of said at least two inlet openings point in an axial direction to said at least one mixer element.

7. The device as in claim 1, wherein at least one of said at least two inlet openings point in a radial direction to said at least one mixer element.

8. The device as in claim 1, further comprising at least one additional redirecting segment disposed adjacent to said at least one first inlet opening, for connecting said second segment with said at least one first inlet opening.

9. The device as in claim 8, wherein said additional redirecting segment extends across an approximately 90° angle.

10. The device as in claim 1, further comprising an insertion coupled to said housing wherein said insertion is aligned transverse to said longitudinal axis of said at least one mixing area and is disposed at a back end of said housing, and wherein said insertion has an inner side turned toward said at least one mixing, area wherein said inner side has uptake recess for receiving said mixer element, and wherein said mixer element further comprises a redirecting element disposed in said uptake recess; and wherein and insertion has an outer side that form at least two inlet supports wherein said at least two ducts extend through said insertion has an outer from said two inlet supports and meet a set of radial openings of said uptake recess via said at least two inlet openings.

11. The device as in claim 1, wherein said at least one first duct and said at least one second duct each have at least two partial ducts that run parallel to each other along with a flow of the at least two compounds wherein said at least partial ducts extend from said at least two coupling openings to their corresponding least two inlet openings of said housing.

12. The device as in claim 1, wherein said at least one mixing element further comprises at least one redirecting element disposed in a region adjacent to said at least two inlet openings wherein said at least one redirecting element is for the feeding of the at least two compounds arriving through at least two inlet openings into said at least one mixing area of said housing wherein said at least one redirecting element has at least one redirecting surface that extends around said longitudinal axis of said at least one mixing area, and runs diagonal to a radial level of said longitudinal axis.

13. The device as in claim 12, wherein said at least one redirecting element is formed in a shape of a wedge.

14. The device as in claim 12, further comprising at least one additional redirecting element, which is disposed around said at least one longitudinal axis diametrically opposite said at least one redirecting element.

15. The device as an claim 12, further comprising at least one additional redirecting element, which is disposed around said at least one longitudinal axis and offset from said at least one redirecting element by an angle of between 90° and 180°.

16. The device as in claim 12, wherein said at least one redirecting surface extends in a form of a helix around said longitudinal axis of said at least one mixing area.

17. The device as in claim 1, wherein said housing has an inner surface defining said at least one mixing area and said at least one mixer element comprises at least two mixer arms including at least one first mixer arm and at least one second mixer arm wherein said at least two mixer arms protrude across several radial levels of said mixer element and extend adjacent to said inner surface of said housing wherein said at least one mixer element comprises an equal number of said at least one first mixer arm and said at least one second mixer arm.

18. The device as in claim 17, wherein said at least one first mixer axis disposed adjacent to said at least one second mixer arm and wherein said at least one first mixer arm is shorter than said at least one second mixer arm.

19. The device as in claim 17, wherein said at least one mixer element further comprises at least one protruding wiper element extending transverse to said at least one longitudinal axis and disposed between a first and a second radial level or said at least two mixer arms.

20. A device according to claim 19, wherein two adjacent mixer arms per radial level are connected to each other through a segment running in the circumferential direction and wherein these pairs of mixer arms connected to each other are arranged offset from each other from a first radial level to a second radial level in the circumferential direction.

21. A device according to claim 20, wherein the arms of said first duct and second duct extending in an axial direction to the inlet openings the mixer area of the housing have a smaller diameter than in its a remaining for said mixer element.

22. A mixing device for mixing at least two compounds in a form of at least one dental mold compound and at least one catalyzing compound for communication with at least one dispensing device having dispensing openings for dispensing the at least two compounds, the mixing device comprising;
    a) a housing having;
        i) at least one mixing area disposed within said housing and extending along a longitudinal axis;

ii) at least one coupling section having:
   a) at least two coupling openings comprising at least a first coupling opening and at least a second coupling opening for coupling with the dispensing opening of the dispensing device,
   b) at least two ducto in communication with said at least one mixing area and comprising at least one first duct and at least one second duct, wherein said at least one first duct has a first segment having an arch shaped cross section extending radially around said longitudinal axis of said at least one mixing area from said at least one first coupling opening; and a redirecting segment coupled to and in communication with said first segment opposite said first coupling opening, and a second segment coupled to and in communication with said redirecting segment, wherein said second segment extends substantially parallel with said longitudinal axis of said at least one mixing area wherein said at least one first duct is formed to extend a flow time of at least one of the at least two compounds in relation to a flow time of at least another of the at least two compounds flowing through said at least one second duct;
iii) at issue two inlet opening comprising at least one first inlet opening and at least one second inlet opening with said at least two inlet openings in fluid communication with said at least one mixing area and said at least one coupling section, for allowing the at least two compounds to flow from at least one first duct and said at least one second duct into said at least one mixing area wherein said redirecting section is further from said at least one first coupling opening than from at least one of said at least two inlet openings;
iv) at least one outlet opening, in fluid communication with said at least one mixing area, for dispensing a mixed compound which is mixed from the at least two compounds in said at least one mixing area; and
   b) at least one mixer element disposed in said mixing area of said housing said at least one mixer element being pivotable about said longitudinal axis of said mixing area;
      wherein the at least two compounds are dispensed from the at least one dispensing device through the dispensing openings, into said at least two coupling openings through said at least two ducts, and said at least two inlet openings wherein the at least two compounds are mixed in said at least one mixing area by said at least one mixer element and then dispensed through said at least one outlet opening.

23. The mixing device as in claim 22, wherein said at least one second further comprises a lengthening section lengthening a flow path from said at least one second coupling opening to said at least one second inlet opening.

24. The device as in claim 22, wherein said first segment and said second segment of said at least one first duct run parallel to each other.

25. The device as in claim 22, wherein said redirecting segment in said at least one first duct and a lengthening segment in said at least one second duct extend around approximately 180° in direction.

* * * * *

UNITED STATES PATENT AND TRADEMARK OFFICE
CERTIFICATE OF CORRECTION

PATENT NO. : 6,837,612 B2
DATED : January 4, 2005
INVENTOR(S) : Bublewitz et al.

It is certified that error appears in the above-identified patent and that said Letters Patent is hereby corrected as shown below:

Column 9,
Line 30, after "arms", change "74" to -- 75 --.
Line 31, "FIG. 3" should read -- FIG. 2 --.
Line 39, after "of" insert -- a --.

Column 12,
Line 30, change "opening" to -- openings --.
Line 32, after "having" change ";" to -- : --.
Line 34, after "along" change "A" to -- a --.
Line 39, after "device" change "," to -- ; --.
Line 58, change "learnt" to -- least --.
Line 64, change "tirot" to -- first --.

Column 13,
Line 3, change "cane" to -- one --.
Line 9, after "openings" insert -- , --.
Line 10, after "openings" insert -- , --.
Line 10, after "ducts" insert -- , --.
Line 25, change "tirot" to -- first --.
Line 40, change "point" to -- points --.
Line 57, after the word "mixing" please delete ",".
Line 58, after "has" insert -- an --.
Line 60, after "wherein" change "and" to -- said --.
Line 63, after "insertion" delete "has an outer".

Column 14,
Line 2, after "compounds" insert -- , --.
Line 2, after "least" insert -- two --.
Line 4, after "corresponding" insert -- at --.
Line 10, after "through" insert -- said --.
Line 41, after "mixer" change "axis" to -- arm is --.
Line 48, after "level" change "or" to -- of --.
Line 55, after "the" change "arms" to -- area --.
Line 56, after "and" insert -- said --.
Line 57, after "openings" insert -- of --.
Line 58, after "in" delete "its".
Line 58, after "remaining" insert -- area --.
Line 66, after "having" change ";" to -- : --.

UNITED STATES PATENT AND TRADEMARK OFFICE
CERTIFICATE OF CORRECTION

PATENT NO. : 6,837,612 B2
DATED : January 4, 2005
INVENTOR(S) : Bublewitz et al.

It is certified that error appears in the above-identified patent and that said Letters Patent is hereby corrected as shown below:

Column 15,
Line 5, change "opening" to -- openings --.
Line 5, after "device" delete "," replace with -- ; --.
Line 6, change "ducto" to -- ducts --,
Line 25, delete "issue" replace with -- least --.
Line 25, change "opening" with -- openings --.

Column 16,
Line 9, after "housing" insert -- , --.
Line 15, after "openings" insert -- ; --.
Line 21, after "second" insert -- duct --.

Signed and Sealed this

Twentieth Day of December, 2005

JON W. DUDAS
*Director of the United States Patent and Trademark Office*